US010543155B2

United States Patent
Tian et al.

(10) Patent No.: US 10,543,155 B2
(45) Date of Patent: Jan. 28, 2020

(54) COMPOSITIONS CONTAINING ZINC SALTS AND ISOTHIOCYANATES FOR REDUCTION OF ORAL VOLATILE SULFUR COMPOUNDS (VSCS)

(75) Inventors: Minmin Tian, Naperville, IL (US); Bryan Hanley, Norwich (GB); Michael Dodds, La Grange Park, IL (US)

(73) Assignee: WM. WRIGLEY JR. COMPANY, Chicago, IL (US)

( * ) Notice: Subject to any disclaimer, the term of this patent is extended or adjusted under 35 U.S.C. 154(b) by 358 days.

(21) Appl. No.: 14/234,517

(22) PCT Filed: Jul. 10, 2012

(86) PCT No.: PCT/US2012/046071
§ 371 (c)(1),
(2), (4) Date: Jun. 4, 2014

(87) PCT Pub. No.: WO2013/015979
PCT Pub. Date: Jan. 31, 2013

(65) Prior Publication Data
US 2014/0294739 A1    Oct. 2, 2014

Related U.S. Application Data

(60) Provisional application No. 61/511,646, filed on Jul. 26, 2011.

(51) Int. Cl.
| | | |
|---|---|---|
| *A61K 8/46* | (2006.01) | |
| *A61K 8/365* | (2006.01) | |
| *A61Q 11/00* | (2006.01) | |
| *A23G 1/32* | (2006.01) | |
| *A23G 3/36* | (2006.01) | |
| *A23G 4/06* | (2006.01) | |
| *A61K 8/27* | (2006.01) | |
| *A61K 8/36* | (2006.01) | |
| *A61K 8/49* | (2006.01) | |

(52) U.S. Cl.
CPC .............. *A61K 8/46* (2013.01); *A23G 1/325* (2013.01); *A23G 3/362* (2013.01); *A23G 4/064* (2013.01); *A61K 8/27* (2013.01); *A61K 8/36* (2013.01); *A61K 8/365* (2013.01); *A61K 8/4973* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 2002/0122843 A1 | 9/2002 | McGrew et al. | |
| 2003/0211209 A1 | 11/2003 | Ekanayake et al. | |
| 2006/0264497 A1 | 11/2006 | Zeligs | |
| 2007/0053849 A1* | 3/2007 | Doyle | A61K 8/02 424/50 |
| 2008/0253976 A1* | 10/2008 | Scott | A61K 8/0216 424/49 |
| 2010/0172941 A1* | 7/2010 | Vajdy | A61K 39/145 424/283.1 |
| 2012/0164268 A1* | 6/2012 | Pearson | A23G 1/50 426/5 |

FOREIGN PATENT DOCUMENTS

| | | | |
|---|---|---|---|
| GB | 2436463 A | | 9/2007 |
| JP | H11246319 A | | 9/1999 |
| JP | 2000086414 A | | 3/2000 |
| WO | WO-00-00166 | * | 1/2000 |
| WO | 0051559 A1 | | 9/2000 |
| WO | 2010140272 A1 | | 12/2010 |

OTHER PUBLICATIONS

Zhang Y, Anticarcinogenic activities of sulforaphane and structurally related synthetic norbornyl isothiocyanates, PNAS, 1994, 91, 3147-3150.*
LKT Laboratories, http://www.lktlabs.com/products/Phenyl_isothiocyanate_Phenyl_mustard_oil-159-48.html, Dec. 31, 2010.*
Keast RSJ, The effect of zinc on human taste perception, Journal of Food Science, 68(5), 2006, 1871.*
Aires et al (J Appl Microbiol, 106 (6), 2086-2094 (Year: 2009).*
Pier Francesco Porciana and Simone Grandini, The Effect of Zinc Acetate and Magnolia Bark Extract Added to Chewing Gum on Volatile Sulfur-Containing Compounds in the Oral Cavity, Journal of Clinical Dentistry, 2012, vol. 23, pp. 76-79, retrieved from www.jclindent.com/Fastrak/FT_23.3_Porciani.pdf on Oct. 6, 2014.
Mintel, "Multi-Nutrient Tablets", retrieved at http:\\www.gnpd.com, Sep. 2010, 4 pages.
Mintel, "Healthy Milk Powder for Woman", retrieved at http:\\www.gnpd.com, Apr. 2006, 2 pages.
Tian, et al., "Chewing gum containing allyl isothiocyanate from mustard seed extract is effective in reducing volatile sulfur compounds responsible for oral malodor," Am. J. Dent., 2013, vol. 26, pp. 180-184.
Eger, et al., "Metal-Mediated Reaction Modeled on Nature: The Activation of Isothiocyanates Initiated by Zinc Thilate Complex," Inorg. Chem., 2011, vol. 50, pp. 3223-3233.

* cited by examiner

Primary Examiner — Celeste A Roney (57) ABSTRACT

Combinations of a zinc salt and an isothiocyanate are provided, and more particularly to a consumer acceptable oral composition containing such combination which is effective in the reduction of volatile sulfur compounds (VSCs).

9 Claims, 4 Drawing Sheets

COMPOSITIONS CONTAINING ZINC SALTS AND ISOTHIOCYANATES FOR REDUCTION OF ORAL VOLATILE SULFUR COMPOUNDS (VSCS)

I. PRIORITY DATA

The present patent application is a 371 of International Application Ser. No. PCT/US12/46071 filed Jul. 10, 2012, which claims benefit from U.S. Provisional Ser. No. 61/511, 646, filed Jul. 26, 2011, and incorporates the above applications by reference herein as if they are fully restated herein.

II. BACKGROUND OF THE INVENTION

This invention relates to an efficacious combination of a zinc salt and an isothiocyanate, and more particularly to an oral composition containing such combination which exhibits increased oral care effects against volatile sulfur compounds (VSCs).

Oral malodor or "halitosis" used herein relates to bad breath caused by physiologic (transient or temporary) and/or pathologic conditions. Physiological causes of halitosis include: halitosis caused by deleterious habits, morning breath, and xerostomia (dry mouth). Pathological causes for halitosis include: secondary or oral tissue conditions associated with gingival and periodontal diseases, acute necrotizing ulcerative gingivitis, residual post-operative blood, debris under dental appliances, ulcerative lesions of the oral cavity, coated tongue, xerostomia, salivary gland diseases and Tonsilloliths (tonsil stones).

Oral malodors are produced mainly due to the breakdown of proteins into individual amino acids, followed by the further breakdown of certain amino acids to produce detectable foul gases. The oral cavity provides a positive growth environment for gram-negative anaerobes that metabolize proteins as an energy source via breakdown of proteinaceous substrates from impacted food particles and sloughed off oral cellular debris. Often, inflammation causes these cells to be shed at a faster rate than the saliva can cleanse. Bacterial action then hydrolyzes the proteins to amino acids; and the amino acids that contain sulfur functional groups, methionine and cysteine, serve as precursors to volatile sulfur compounds (VSCs).

These gaseous volatile sulfur compounds (VSCs) are responsible for oral malodor, and consist primarily of hydrogen sulfide ($H_2S$), methyl mercaptan ($CH_3SH$) and dimethyl sulfide [$(CH_3)_2S$]. For example, amino acids methionine and cysteine are reduced to hydrogen sulfide and methyl mercaptan, respectively, in the presence of sulfhydrase-positive microbes. Methyl mercaptan has been found to be the main component of tongue dorsal surface malodor in patients with periodontal disease, whereas hydrogen sulfide predominates in orally healthy subjects.

Although bad breath primarily represents a source of embarrassment or annoyance, the VSCs most responsible for halitosis are also potentially damaging to the tissues in the mouth, and can lead to periodontitis (inflammation of the gums and ligaments supporting the teeth). In particular, VSCs have been found to damage the collagen and proteoglycan components in connective tissue by cleaving disulfide bonds. This de-aggregation of the extracellular matrix allows microbes to permeate the oral mucosa. As bacteria further accumulates in pockets that form next to the teeth, periodontal disease progresses, as well as halitosis. If the periodontal disease advances significantly, overall systemic health may be jeopardized; for example, periodontal bacterial by-products can enter the blood stream and may result in heart disease, stroke and under-weight babies at birth.

For the treatment of oral malodor, the public has increasingly turned to commercially available mouth-freshening products. The market for these products has been growing continuously as sufferers from chronic oral malodor experience personal discomfort and social embarrassment.

Various compounds such as chlorine dioxide, sodium chlorite, and metal salts such as zinc and copper have been used as VSC neutralizing agents in a variety of oral compositions. Such compounds have been provided and are available today as mouthwashes and rinses for the prevention and/or treatment of oral malodor. In general, many of the oral rinses available today are used for the prevention and/or treatment of oral malodor or halitosis, but for chronic bad breath, many rinses offer little to no help.

While being effective in fighting oral malodor, compounds such as chlorine dioxide, sodium chlorite, and metal salts such as zinc and copper impart strong, unpleasant flavors and aromas thereby negatively impacting taste and deterring use. Often, mouth rinses incorporating these compounds can also cause some generalized irritations to the oral cavity such as desquamation, ulceration, and inflammation. Moreover, oral compositions incorporating these compounds (other than mouthwashes and rinses) which are retained in the mouth for longer periods of time, such as chewing gums, mints, and lozenges, further enhance irritations to the oral cavity when these compounds are employed.

Alternatively, isothiocyanates can also act as a reagent to remove both intrinsic and extrinsic VSC's, either by conversion of sulfur groups (SH) into the water soluble dithiocarbamate or by formation of the less volatile disulfide. Unfortunately at certain concentrations, isothiocyanates possess a pungent or irritating odor, and sharp bitter taste. Because of the unpleasant organoleptic attributes, using isothiocyanates in oral compositions is difficult.

In view of the preceding challenges, there is a continued need to develop an effective treatment for oral malodor caused by physiologic and/or pathologic conditions. Accordingly, the dental community, as well as the general public, are continuously seeking efficacious, commercially available, and organoleptically pleasing oral compositions to reduce various types of bad breath (halitosis), including occasional, chronic, or at specific times of the day.

Thus, it would be highly advantageous, to have an efficacious, commercially available, and organoleptically pleasant product solution for oral malodor.

III. SUMMARY OF THE INVENTION

An oral composition containing an effective combination of a zinc salt and an isothiocyanate to reduce volatile sulfur compounds (VSCs) in the oral cavity. Moreover, methods for reducing volatile sulfur compounds are also provided.

V. DESCRIPTION OF THE INVENTION

The present invention relates to an unlikely combination of metal salts and isothiocyanates, effective against multiple volatile sulfur compounds (VSCs) present in the oral cavity. Further, the levels of the metal salts and the isothiocyanates used in combination with one another as described in relation to the invention are lower than each used individually. Accordingly, Applicants invention provides efficacious oral compositions in reducing VSCs, thereby reducing oral malodor.

As used herein, the term "efficacious" means producing or capable of producing a desired effect. Moreover, "effective amount" refers to the level, amount, serving, or percent which produces or is capable of producing a desired effect. All percentages and ratios used herein are by weight of the total composition and all measurements made are at 25° C., unless otherwise designated.

Zinc salts are incompatible with consumer taste acceptance criteria, effective only for short periods of time or not effective at all in reducing certain volatile sulfur compounds, such as methyl mercaptan ($CH_3SH$) when used individually.

Isothiocyanates are volatile compounds, and are classified as either an oral or nasal irritant, or both. The pungent sensations of isothiocyanates may be sensed throughout the oral mucosal tissues, including the upper respiratory tract.

As described in more detail below, the invention provides continued breath freshening after consuming or masticating the oral composition. For example, breath freshening benefits will last for at least about 15 minutes, typically for at least about 30 minutes, and preferably for at least about 60 minutes after consumption or mastication of the oral composition. Typically, breath freshening will continue after consumption or mastication for at least about 60 minutes, maintaining a total VSC reduction of at least 50%. As used herein, "total VSC" includes two or more of the following VSCs: hydrogen sulfide ($H_2S$), methyl mercaptan ($CH_3SH$) and dimethyl sulfide [$(CH_3)_2S$] in any combination. In other embodiments, breath freshening benefits will continue after 120 minutes with a total VSC reduction of at least 40% and preferably after 180 minutes with a total VSC reduction of at least 20% after consumption or mastication of the oral composition.

In particular, various embodiments of the invention provide an effective amount of zinc lactate, zinc gluconate, zinc ascorbate, or zinc aspartate and mixtures thereof, in combination with an isothiocyanate to inhibit or ameliorate multiple volatile sulfur compounds in an oral composition at a combined concentration of less than 0.50% by weight.

An oral composition of the present invention can take any physical form suitable for application to an oral surface of humans, dogs, cats, or other animals and provides either a cosmetic prophylactic or therapeutic benefit within or derived from the oral cavity. In various embodiments, an oral composition of the invention can be a dentifrice such as a powder or paste; an edible film or bioadhesive film; a confectionary composition including but not limiting to breath mints, low boiled candy, chewing gum, chewy candy, hard boiled candy, coated candy, lozenges, syrups, pressed mints, throat drops, and chocolates; pet foods, chews or biscuits and the like. In certain embodiments, the consuming or masticating of the oral composition may be repeated at regular intervals.

Applicants have identified suitable, efficacious, and consumer acceptable levels of including both zinc salts and isothiocyanates for use in various oral compositions to reduce multiple VSCs in the oral cavity.

Zinc Salts

As previously suggested in accordance with various embodiments of the invention, an effective amount of a zinc salt may be used to inhibit volatile sulfur compounds in the oral cavity, thereby reducing oral malodor. Examples of organic zinc salts for VSC reduction include zinc gluconate (average zinc ion content of 12.8%), zinc lactate (average zinc ion content of 23.2%), zinc ion acetate (average zinc ion content of 29.8%), and zinc citrate (average zinc ion content of 32.2%); although based on the Applicants' research (as provided in more detail below), not all zinc salts are effective against all types of VSCs. Under normal circumstances, zinc salts containing a high level of zinc ion perform better than a zinc salt containing low level of zinc ion.

Suitable zinc salts for use in these formulations include zinc acetate (molar solubility in water of 1.64 moles/l), zinc citrate (molar solubility in water of <0.1 moles/l), zinc gluconate (molar solubility in water of 0.28 moles/l), and zinc lactate (molar solubility in water of 0.17 moles/l). Normally, a zinc salt with better water solubility performs better than a zinc salt with poor water solubility.

Metal salts such as zinc salts have the ability to chelate VSCs present in the oral cavity and form non-volatile metal ion-sulfide complexes, thereby neutralizing oral malodor. However, this ability to neutralize oral malodor is temporary. The metal salts do not change mouth conditions, and do not exhibit activity against odor producing bacteria present in the oral cavity. Accordingly, oral hygiene products containing zinc salts, such as zinc chloride mouthwashes, are considered by some to be effective for halitosis, but for many, they are not effective and only have temporary effects.

Figure 1:
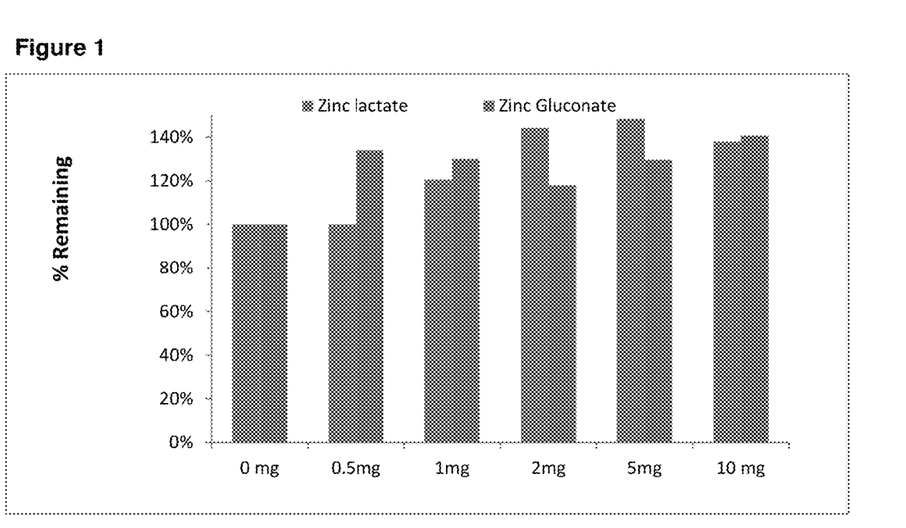
FIG. 1 is an illustration of the change of headspace concentration of CH3SH after addition of zinc lactate or zinc gluconate.

In general, Applicants have identified that some zinc salts are not effective against all VSCs, such as hydrogen sulfide ($H_2S$), dimethyl sulfide [$(CH_3)_2S$], and methyl mercaptan ($CH_3SH$), but instead may only be effective against specific VSCs. For evaluation of the efficacy of various zinc salts against specific VSCs, the Applicants established an in vitro method using a headspace gas-chromatograph equipped with a sulfur detector. Thus, a total of 200 ppm of $CH_3SH$ in 5 ml of phosphate buffer solution (PBS) was prepared. The pH was maintained at 7.4. Different amounts of zinc lactate or zinc gluconate were added into the test tube and mixed for 5 minutes at 37° C. The headspace sample was injected into a gas chromatograph sulfur chemiluminescence detector (GC-SCD). FIG. 1 below shows the testing result.

As shown in FIG. 1, Applicants identified that both zinc lactate and zinc gluconate were ineffective in reducing the headspace concentration of methyl mercaptan ($CH_3SH$). In fact, Applicants observed that zinc salts tested increased the volatility of $CH_3SH$ by 10-40%.

Figure 2:
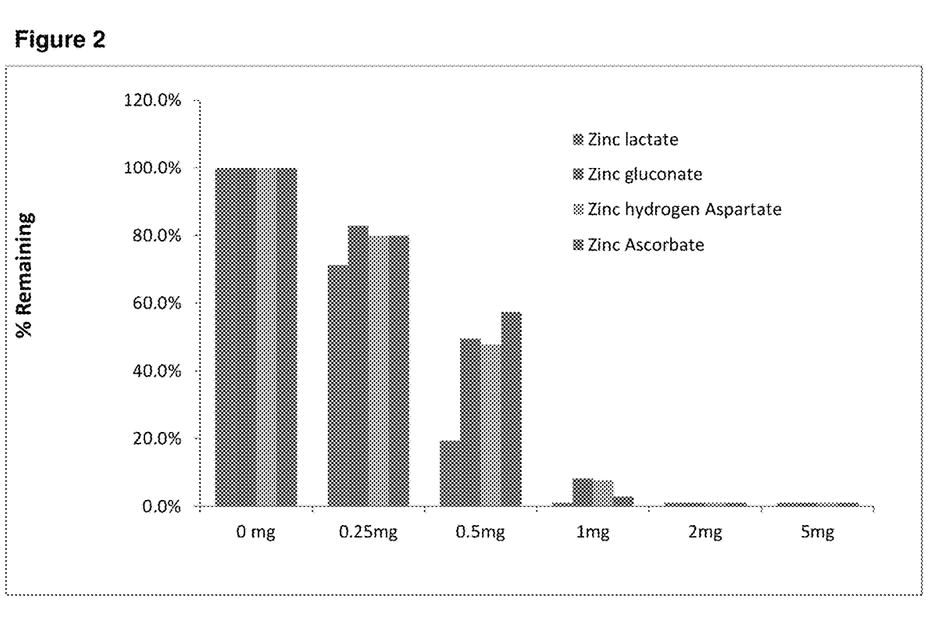
FIG. 2 is a graphical representation of the change of headspace concentration of H2S after addition of zinc salts analyzed by GC-SCD.

In another experiment, 5 ml of PBS solution containing 1 mg of $H_2S$ was prepared via a serial dilution in a 22 ml headspace vial for FIG. 2 below. Different amounts of zinc salts were added and mixed at 37° C. for 5 min. The headspace concentration of H$_2$S was analyzed by GC-SCD. FIG. 2 shows the testing results.

As shown in FIG. 2, Applicants have identified that zinc gluconate, zinc lactate, zinc hydrogen aspartate, and zinc ascorbate reduces the oral malodor produced by hydrogen sulfide (H$_2$S).

More significantly, zinc lactate reduces H$_2$S at concentrations greater than 0.25 mg, and zinc gluconate, zinc hydrogen aspartate, and zinc ascorbate at concentrations greater than 0.5 mg in vitro.

Thus, Applicants surprisingly found that neither zinc lactate nor zinc gluconate reduced the headspace concentration of the volatile sulfur compound methyl mercaptan (CH$_3$SH), which is a more offensive and sensitive odorant compared to hydrogen sulfide (H$_2$S).

Unfortunately, while being effective against some VSCs, salts of metal cations such as aluminum sulfate and zinc chlorite, zinc lactate, zinc acetate, and the like, are often unpleasant or unpalatable to many consumers. Due to this undesirable effect caused by products containing metal salts, and in consideration of the temporary halitosis neutralization benefits, consumer motivation to purchase and use products containing these ingredients in the treatment of oral malodor is low.

Isothiocyanates

Isothiocyanates are volatile compounds, and are classified as either an oral or nasal irritant, or both. The pungent sensations of isothiocyanates may be sensed throughout the mucosal tissues of the mouth as well as in the upper respiratory tract. Isothiocyanates are bound as precursors in whole vegetables and are released through enzymatic action when the plant materials are ground. Isothiocyanates are biologically active hydrolysis (breakdown) products of glucosinolates. Cruciferous vegetables such as broccoli, cauliflower, kale, turnips, collards, brussel sprouts, cabbage, kohlrabi, rutabaga, Chinese cabbage, and bok choy contain a variety of glucosinolates, each of which forms a different isothiocyanate when hydrolyzed and is illustrated in FIG. 3.

For example, broccoli is a good source of glucoraphanin, the glucosinolate precursor of sulforaphane (SFN), and sinigrin, the glucosinolate precursor of allyl isothiocyanate (AITC). Watercress is a rich source of gluconasturtiin, the precursor of phenethyl isothiocyanate (PEITC), while garden cress is rich in glucotropaeolin, the precursor of benzyl isothiocyanate (BITC). Studies have shown that these compounds are responsible for the unpleasant taste of cruciferous vegetables, raw or cooked.

Horseradish and mustard share the common family of isothiocyanates as pungent principles. Allyl isothiocyanate (AITC), which occurs in both mustard and horseradish, is the most common member of this family. Brown mustards contain 3-butenyl isothiocyanate. *Brassica* glucosinolates, otherwise known as mustard oil glycosides, tend to be bitter.

Figure 3:
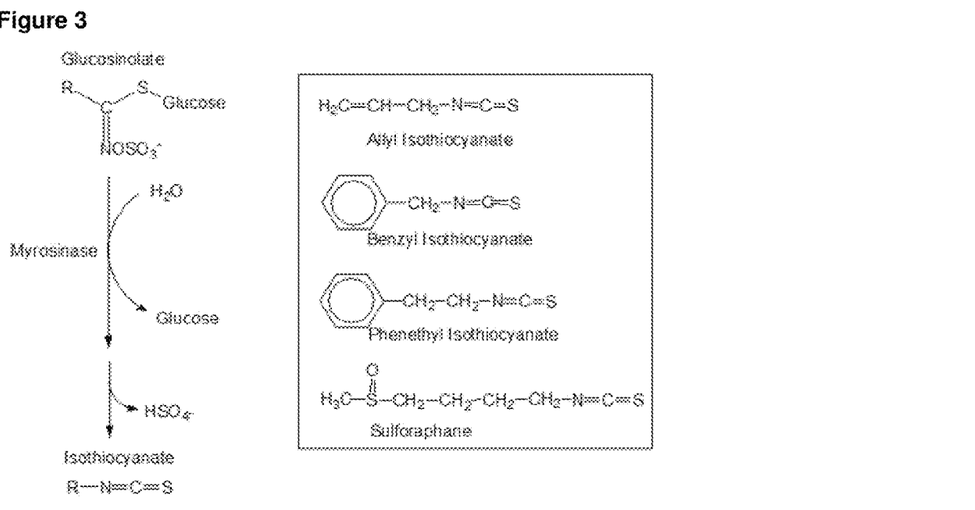
FIG. 3 is an illustration of the different forms of isothiocyanate that result from hydrolyzing glucosinolates.

Natural Isothiocyanates useful in this invention include the following myrosinase-catalyzed glucosinolate compounds from the plant family Brassicaceae: sulforaphane (SFN), allyl isothiocyanate (AITC), phenethyl isothiocyanate (PEITC), benzyl isothiocyanate (BITC), as shown in FIG. 3. Preferable natural isothiocyanates useful in this invention are allyl isothiocyanates, also known as mustard oils, and commonly found in horseradish, and wasabi. As described herein, the term "natural" means a chemical compound or substance produced by a living organism and found in nature, which may possess a pharmacological or biological activity for use in pharmaceutical drug discovery and drug design. A product may be considered as "natural" although the product is prepared by total synthesis if the components are substantially identical to a substance found in nature.

Examples of synthetic or non-natural isothiocyanates include 3-morpholinopropyl isothiocyanate, phenylisothiocyanate, and norbornyl isiocyanate ([endo-2-acetyl-exo-6-isothiocyanatonorbornane, exo-2-acetyl-exo-6-isothiocyanatonorbornane, exo-2-acetyl-exo-5-isthiocyantonorbornane], which can be synthesized from sulforaphane or from commercially available 2-acetyl-5-norbornene). Applicants tested a variety of isothiocyanates against the volatile sulfur compound, hydrogen sulfide (H$_2$S).

A stock solution of H$_2$S was prepared by a serial dilution in PBS buffer (pH 7.4), with a final concentration of 200 ppm. Allyl isothiocyanate, benzyl isothiocyanate, ethyl isothiocyanate and 3-methylthiopropyl isothiocyanate (all from Sigma-Aldrich) were dissolved in pure ethanol to form 1.0% of working solution of each. A total of 5 ml PBS buffer containing 200 ppm of H$_2$S in a headspace vial (22 ml volume) was mixed with 0.125, 0.25, 0.5 and 1 mg of each isothiocyanate compound for 5 min at 37° C., respectively. The headspace sample was injected into the GC-SCD by an automatic sampler for VSC analysis. The reduction of headspace concentration of H$_2$S was calculated by the formula below:

$$\% \text{ H}_2\text{S reduction} = \frac{\text{(Peak area before mixing)} - \text{(Peak area after mixing)}}{\text{(Peak area before mixing)}} \times 100\%$$

TABLE 1

In vitro reduction of hydrogen sulfide (H$_2$S) by allyl isothiocyanate, benzyl isothiocyanate, ethyl isothiocyanate and 3-methylthiopropyl isothiocyanate:

| Sample | Amount | Peak Area | % Reduction of headspace concentration |
|---|---|---|---|
| Control | 200 ppm | 853223827 | 0% |
| Allyl isothiocyanate | 50 ppm | 431713256 | 49% |
|  | 100 ppm | 13651581 | 98.4% |
|  | 200 ppm | 4266119 | 99.5% |
| Benzyl isothiocyanate | 25 ppm | 491908604 | 42% |
|  | 50 ppm | 398519292 | 53% |
| Ethylisothiocyanate | 50 ppm | 963110533 | −13% |
|  | 100 ppm | 726258436 | 14.9% |
|  | 200 ppm | 271822727 | 68% |
| 3-methylthiopropyl isothiocyanate | 50 ppm | 416687277 | 51% |
|  | 100 ppm | 211177117 | 75% |
|  | 200 ppm | 46897168 | 94.5% |

Table 1 above indicates that the isothiocyanates tested aid in reducing hydrogen sulfide (H$_2$S). At 50 ppm, benzyl isothiocyanate demonstrated a reduction of H$_2$S of greater than 50%. More significantly, ethylisothiocyanate reduced the headspace of H$_2$S by 68% at 200 ppm; 3-methylthiopropyl isothiocyanate reduced the headspace of H$_2$S by 75% at 100 ppm, and 94.5% at 200 ppm. In particular, allyl isothiocyanate (AITC) showed a strong reduction of H$_2$S (greater than 90% at 100 ppm or greater).

However, to provide the efficacious levels as shown above in an oral composition, this would impart strong, unpleasant tastes, and would not be organoleptically pleasing.

In view of the results pertaining to allyl isothiocyanate in Table 1, Applicants further evaluated allyl isothiocyanate in vitro for its VSC elimination effect of hydrogen sulfide ($H_2S$). A 20 ml headspace vial containing 5 ml of PBS solution and 200 ppm of $H_2S$ was treated with various concentrations of allyl isothiocyanate, respectively (0.25-1.0 mg). In a standard experimental protocol, a stock of hydrogen sulfide solutions were prepared by dissolving c.a. 0.10 g of sodium sulfide in a total of 10 ml phosphate buffer solution (PBS) (pH 7.4). It was further diluted in PBS to produce a working solution contained 200 ppm of $H_2S$ in buffer.

TABLE 2

In vitro reduction of hydrogen sulfide ($H_2S$) by allyl isothiocyanate (AITC)

| Allyl isothiocyanate | Reduction of $H_2S$ |
|---|---|
| 0 mg | 0.0% |
| 0.25 mg | 49.0% |
| 0.5 mg | 98.4% |
| 1 mg | 99.5% |

Table 2 indicates that allyl isothiocyanate (AITC) reduces oral malodor associated with hydrogen sulfide ($H_2S$) at concentrations greater than 0.25 mg (or 50 ppm) in vitro.

In view of the preceding efficacy identified in vitro (Tables 1 & 2), allyl isothiocyanate (AITC) was further evaluated for in vivo breath freshening effects. Chewing gum containing 100 ppm of allyl isothiocyanate (AITC) was prepared in the laboratory, and was rolled, sheeted, and cut into sticks with a weight average of 2.7 g. A randomized, double-blind clinical study was conducted for evaluation of chewing gum containing allyl isothiocyanate (AITC). A total of 15 subjects met inclusion and exclusion criteria were recruited and completed the study. Subjects were instructed to refrain from oral hygiene, eating and drinking to the testing site. Each subject exhaled his/her breath to a gas chromatograph to analyze for baseline (before treatment, t=0) VSC. Subjects then chewed 1 dose of experimental gum (or control gum) for 12 minutes. Subject exhaled his/her breath to the gas chromatograph immediately after chew, and 60, 120, and 180 minutes. Each test was repeated twice. There were at least two days between treatments.

TABLE 3

In vivo reduction of $H_2S$ using chewing gum containing 100 ppm of allyl isothiocyanate (AITC)

| | Gum-base[1] (no AITC, flavor, or sweeteners) | Control gum (no AITC) | Experimental (100 ppm AITC) |
|---|---|---|---|
| Baseline | 0% | 0% | 0% |
| Immediate after chew | 1% | 39% | 60%† |
| 60 min | −10% | 10% | 28% |
| 120 min | −35% | −18% | 23% |
| 180 min | −39% | −20% | 2% |

[1]Results from previous study
†Statistical significant compared with baseline
*Statistically significant compared with control gum Table 3 shows that chewing gum containing 100 ppm AITC-gum reduces oral malodor associated with hydrogen sulfide ($H_2S$), over the control gum and baseline (pre-treatment, t=0); the results were significant (p>0.05) when compared with baseline results immediately after chewing. Further, when compared to the in vitro hydrogen sulfide ($H_2S$) testing reflected in Table 2, AITC appears less efficacious when applied to chewing gum compositions.

TABLE 4

In vivo reduction of $CH_3SH$ using chewing gum containing 100 ppm of allyl isothiocyanate (AITC)

| | Gumbase[1] (no AITC, flavor, or sweeteners) | Control gum (No AITC) | Experiemental gum (100 ppm AITC) |
|---|---|---|---|
| Baseline | 0% | 0% | 0% |
| Immediate after chew | 8% | 56%† | 73%† |
| 60 min | −24% | 3% | 46%† |
| 120 min | −110% | −64% | 32% |
| 180 min | −90% | −73% | 12% |

[1]Results from previous study
†Statistical significant compared with baseline
*Statistically significant compared with control gum The date of Table 4 above shows that the experimental AITC-gum reduces $CH_3SH$ associated with oral malodor, over the control gum and baseline (pre-treatment, t=0); the results were significant (p>0.05) when compared with both the control gum and baseline immediately after chewing, and after 60 min when compared to baseline result.

In light of the decreased efficacy of AITC found in vivo when compared to the in vitro results, Applicants tested allyl isothiocyanate for its ability to release from chewing gum. One piece of gum (piece weight: 2.7 g) containing 0.27 mg of allyl isothiocyanate were chewed for 20 minutes and the residual gum cud analyzed by gas chromatography. Results were compared with extraction of unchewed gum from which recovery was 48.5%. The release of allyl isothiocyanate from the gum was found to be 69.6% after 20 minutes of chewing.

While isothiocyanates such as allyl isothiocyanate show ability in reducing VSCs (such as $H_2S$), those skilled in the art recognize that isothiocyanates impart pungent aroma, spicy, bitter taste, and are irritating to both the oral and the mucous membranes; even when consumed at low levels. The levels shown to be efficacious would impart unpleasant taste and other negative organoleptic properties to a consumer. It is understood that the effective concentrations of isothiocyanates demonstrated is constrained by the need to provide oral malodor reduction without adversely affecting the appearance, taste, color or texture of various oral compositions.

Combination of Zinc Salts and Isothiocyanates

In accordance with the present invention, combinations of metal salts and isothiocyanates have been found effective against multiple volatile sulfur compounds (VSCs) present in the oral cavity. Further, the combination and levels described herein are lower than if used individually, providing consumer acceptable and efficacious oral compositions in reducing VSCs, thereby reducing oral malodor.

As established above, when used individually, zinc salts or isothiocyanates may be effective for short periods of time or not effective at all in reducing certain volatile sulfur compounds (such as methyl mercaptan ($CH_3SH$)). Applicants combination of both compounds provide for efficacious amelioration of multiple VSCs for extended periods of time, even post-mastication or consumption. Moreover, the combination of metal salts and isothiocyanates yield an organoleptically pleasing taste that is acceptable by consumers compared to when each of the compounds are used individually, at higher levels.

Compositions useful to the invention comprise a zinc salt and a compound extracted from mustard oil, such as such allyl isothiocyanate, ("AITC") or a synthetic or semi-synthetic equivalent of such a component or compound thereof. Typically, AITC may be extracts of mustard oils.

The relative combination of the zinc salt and isothiocyanate to one another provide the desire effects of Applicants invention. More particularly, an effective concentration of zinc lactate and allyl isothiocyanate in an oral composition of this invention depends not only upon the relative concentration at which enhancement of activity against volatile sulfur compounds is achieved, but also when a consumer acceptable taste is provided. In an aspect of the invention, an enhanced weight ratio of zinc salt/isothiocyanate in an oral composition is at least 0.1:1, typically at least 0.5:1 and preferably at least 1:1. This weight ratio may range up to 100:1 or above, typically up to 1:1, preferably up to 10:1. A typical weight ratio range is between 0.5:1 to about 50:1 and preferably 1:1 to 20:1.

In an embodiment, the ratio of zinc salt to isothiocyanate is between 1:1 to about 20:1 wherein the zinc salt is an organic zinc salt, and the isothiocyanate is allyl isothiocyanate.

In other embodiments of the invention, the zinc salt is present in the oral composition in an amount of about 0.001 to about 0.50 wt. %. Such a concentration is dependent upon the concentration of the isothiocyanate employed for enhanced results against volatile sulfur compounds (VSCs). In one embodiment, the zinc salt is present in the oral composition in an amount of about 0.001 to about 1 wt. %. In other embodiments, the zinc salt is present at less than 0.50 wt. %, for example the zinc salt is present at a concentration of in an amount of about 0.01 to about 0.25 wt. %. In one preferred embodiment, zinc lactate is present in the oral composition at a concentration of about 0.10 wt. %. Overall, the concentration of zinc salt is below a level which produces an objectionable taste.

The zinc salt may be a commonly used organic zinc salt, including zinc gluconate, zinc lactate, zinc acetate, zinc citrate, and combinations thereof.

Still further, the isothiocyanate is present in the oral composition in an amount of about 0.001% to about 1 wt. %. In other embodiments, the isothiocyanate present at less than 1%. In one preferred embodiment, the allyl isothiocyanate is present in the oral composition at a concentration of about 0.01 wt. %. Allyl isothiocyanate may be determined by a gas chromatograph-mass spectrophotometer (GC-MS). The isothiocyanate may be natural or non-natural, including but not limiting to sulforaphane (SFN), allyl isothiocyanate (AITC), phenethyl isothiocyanate (PEITC), benzyl isothiocyanate (BITC), 3-morpholinopropyl isothiocyanate, phenylisothiocyanate, and norbornyl isiocyanate ([endo-2-acetyl-exo-6-isothiocyanatonorbornane, exo-2-acetyl-exo-6-isothiocyanatonorbornane, exo-2-acetyl-exo-5-isthiocyantonorbornane], which can be synthesized from sulforaphane or from commercially available 2-acetyl-5-norbornene), alone or in any combination.

Oral compositions useful in this invention contain a VSC reducing effective amount of a zinc salt and an isothiocyanate combined with a suitable carrier. A suitable carrier typically is a food-acceptable or food contact acceptable material in which the zinc salt and isothiocyanate used in the invention may be incorporated or dispersed without adverse effect. A typical suitable carrier is a water-soluble solid or chewable solid such as a confectionery composition. Another suitable carrier is a dentifrice such as a past or powder. Other suitable carriers for cats, dogs and other animals include but are not limited to chews, biscuits, kibble (dry), and canned (wet/soft) pet foods.

The term "confectionery composition" as used herein includes chewing gums, and orally soluble tablets, beads and lozenges. Saliva dissolves the lozenge or chewable gum product, and promotes prolonged contact with oral surfaces so that the delivery of the VSC reducing agents in a lozenge tablet, bead or chewing gum form ensures that an adequate dosage of the active ingredients are delivered to the oral surface when the product is used. Or, the confectionery composition may be in the form of a coating, shell, film, syrup or suspension.

In an embodiment, an oral composition is a chewing gum composition which is suitable for chewing and which comprises 2% or greater, by weight of the composition, of elastomer. In general, chewing gum compositions are chewed or masticated by consumers, the process by which food is mashed and crushed by teeth. Such chewing gum compositions can take a variety of shapes and forms, for example, a pellet, a gumball, a square, a stick, etc., and may be coated by a variety of materials including but not limiting to sugars, polyols, chocolates, syrups, films, and the like, alone or in any combination. Natural or artificial colors and combinations thereof, high intensity sweeteners and flavors may also be added to the coating solution. For pellet or coated chewing gums, zinc salts may be incorporated in a coating or in a center.

A chewing gum useful to the invention is a sugarless chewing gum containing a zinc salt and an isothiocyanate to reduce VSCs. Chewing gum formulations typically contain, in addition to, a chewing gum base, one or more plasticizing agents, at least one sweetening agent and at least one flavoring agent.

In accordance with an embodiment, a chewing gum is provided containing zinc lactate from about 0.002% to about 2% by weight, and allyl isothiocyanate from of 0.001% to about 5% by weight, wherein the chewing gum provided a reduction in multiple VSCs up to 180 minutes after chewing.

In an aspect of the invention, a chewing gum composition is provided wherein the zinc salt is at a concentration of about 0.10% by weight, and the isothiocyanate is at a concentration of about 0.01% by weight. The isothiocyanate provided may comprise multiple isothiocyanates, natural or non-natural, and combinations thereof. The chewing gum is masticated for at least 5 minutes, for at least 10 minutes, or for at least 15 minutes. Total VSC reduction occurs immediately after post-mastication, or for at least 30 minutes, 60 minutes, typically for at least 90 minutes, and preferably for at least 120 minutes.

In an embodiment, the allyl isothiocyanate has at least 50% release from a chewing gum into the oral cavity of the user.

In another embodiment, a hard sugarfree candy is provided, containing less than 0.50% by weight zinc salt, and less than 1% by weight isothiocyanate.

While not limiting to theories by which the present invention is bound, it is generally believed that a minimum enhanced effective anti-volatile sulfur compound level (VSC) of zinc salt is between about 100 µg/mL (100 mg/kg or parts per million (ppm)) to about 2500 µg/mL (2500 ppm) and the isothiocyanate concentration is between 10 µg/mL (10 ppm) to about 1000 µg/mL (1000 ppm) against VSCs in an oral composition.

In an embodiment, the level of allyl isothiocyanate is less than 50 ppm in an oral composition.

In a preferred embodiment, an effective enhanced breath freshening level of zinc lactate against VSCs is between 100

μg/mL to about 2000 μg/mL and the isothiocyanate is selected from the group consisting of allyl isothiocyanate, benzyl isothiocyanate, phenethyl isothiocyanate, and sulforphane, wherein the level of isothiocyanate is between 10 μg/mL to about 500 μg/mL.

In an aspect of the invention an oral suspension is provided wherein a zinc salt is provided at about 1250 μg/mL, and the non-natural isothiocyanate is provided at about 1000 μg/mL.

Figure 4:
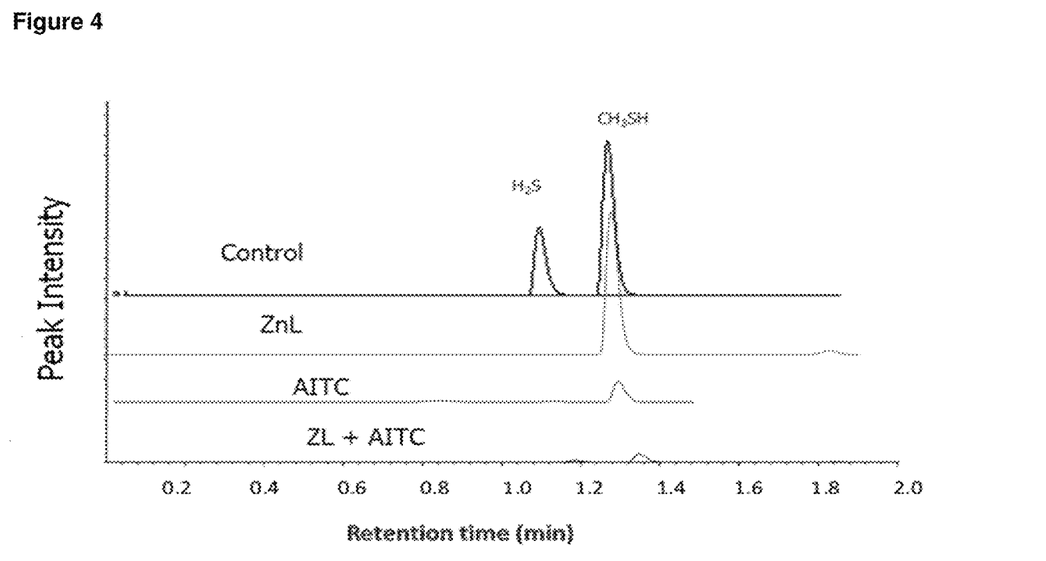
FIG. 4 is a graphical representation of Peak Intensity vs. Retention Time (min) from injecting the headspace sample into a GC column with an SCD detector.

I. Data a. Combination of Zinc Lactate and Allyl Isothiocyanate (AITC) Against Multiple VSCs: $H_2S$ and CH3SH Method: A mixture of hydrogen sulfide ($H_2S$) and methyl mercaptan ($CH_3SH$) was prepared by mixing 5 parts of $H_2S$ and 1 part of $CH_3SH$ in an aqueous phosphate buffer solution (PBS) at pH 7.4. The final concentrations of $H_2S$ and $CH_3SH$ in solution were a 200 and 40 ppm, respectively. The final amount of VSC was 1.2 mg in the test vial. Although the headspace concentrations of $H_2S$ and $CH_3SH$ were well above the level found in a typical foul mouth air (200-500 parts per billion), the total amount of VSC was close to the amount presented in oral cavity. Subsequently, 5 ml of the VSC mixture was kept in a 22 ml tight screw cap headspace vial at 37° C. for 5 min. The headspace sample was injected into a GC column with an SCD detector. FIG. 4 below shows the testing result (control). The large peak area of $CH_3SH$ reflects its volatility in the headspace compared with $H_2S$.

Separately, 1 mg of zinc lactate, or 1 mg of allyl isothiocyanate (AITC), or combination of 1 mg Zinc lactate and 1 mg of AITC were added to each of headspace vial containing 5 ml VSC mixture and equilibrated at 37° C. for 5 min. Each headspace sample was injected into a GC column by a Combi-Pal auto-sampler. The amount of sulfur was analyzed by an Agilent SCD-355 chemoluminescent sulfide detector.

FIG. 4 demonstrates allyl isothiocyanate (AITC) and zinc lactate (ZnL or ZL) exhibit an enhanced effect on multiple VSCs ($H_2S$ and CH3SH); 1 mg of AITC eliminates 98% of $H_2S$ and 78% of $CH_3SH$; 1 mg of ZL eliminates 98% of $H_2S$, 0% of $CH_3SH$.

b. Expert Panelist Evaluation of Taste & Sensory of AITC-ZL Gum

Figure 5:
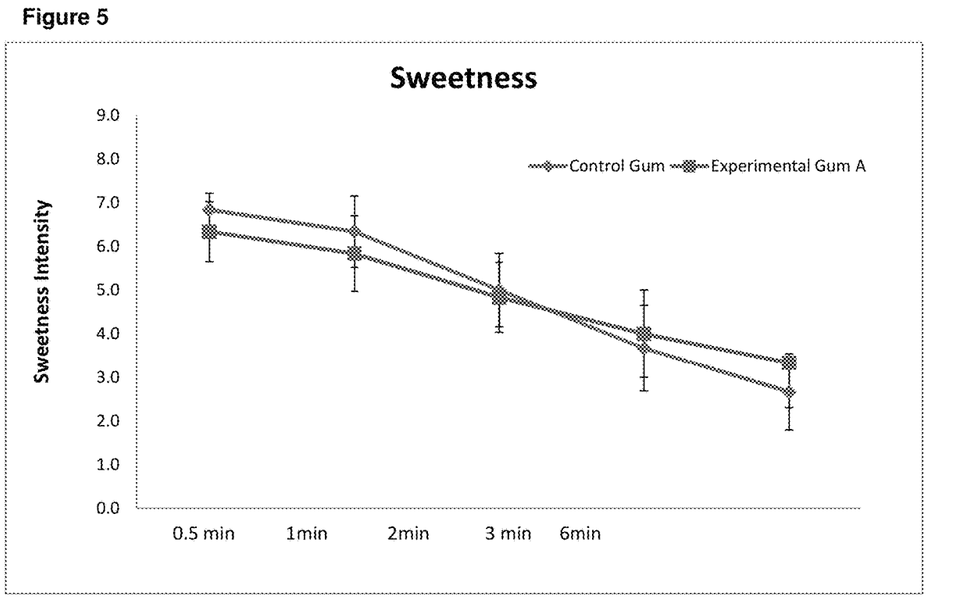
FIG. 5 is a graphical representation of Sweetness Intensity vs. Time (min) for the Control Gum and Experimental Gum A.
Figure 6:
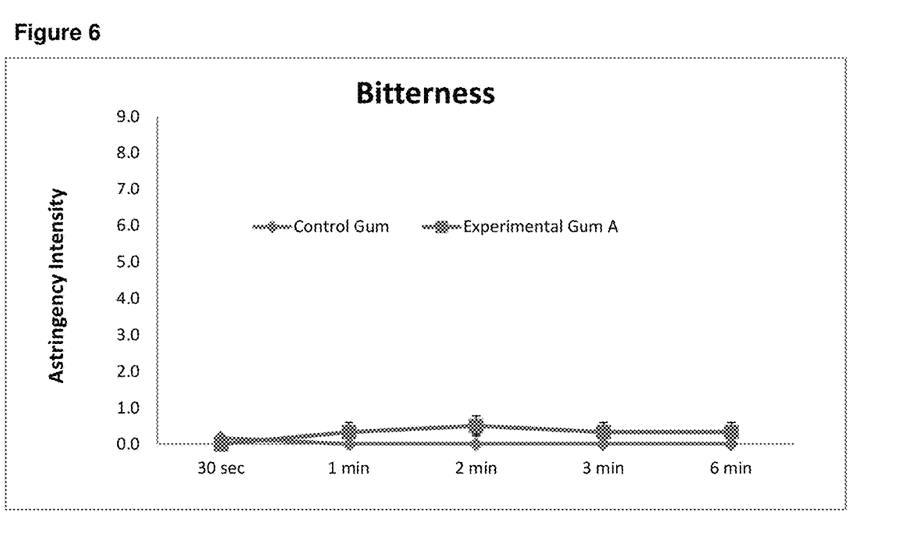
FIG. 6 is a graphical representation of Bitterness Astringency Intensity vs. Time (min) for the Control Gum and Experimental Gum A.
Figure 7:
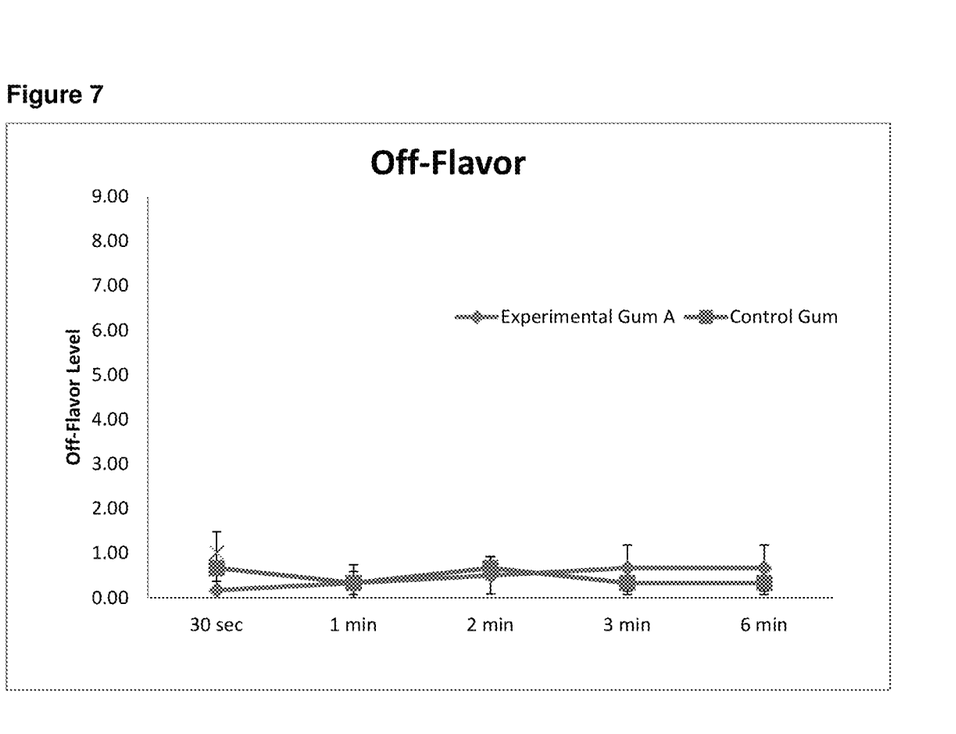
FIG. 7 is a graphical representation of Off-Flavor Level vs. Time (min) for the Control Gum and Experimental Gum A.

To evaluate the sensory and taste acceptance of the AITC-Zinc gum, an ESA (Expert Sensory Analysis) test was conducted with total of 6 internally trained expert panelists. Each panelist chewed the control gum, or the experimental gum for 6 min. The control gum contained no AITC, and the experimental gums contained 0.01% (100 ppm) of AITC and 0.1% (1000 ppm) of zinc lactate as shown below in Table 5. The panelist evaluated the sweetness intensity, bitterness intensity and off-flavor notes in a 9 point scale (0—lowest intensity; 9—highest intensity). FIGS. 5-7 below show the testing results:

For the following chewing gum preparations below, gum base was heated to 85° C. in a gum mixer. Zinc lactate, sorbitol, intense sweeteners, glycerin and sorbitol syrup were added to the warmed gum base. Allyl-isothiocyanate (AITC) was added to the flavor and stirred well before added to the gum mixer. After addition of the remaining gum ingredients, the gum bolus was sheeted and cut to sticks. Each stick gum weighs 2.7 gram. Table 5 below shows the formulas of experimental gum:

TABLE 5

| Ingredient | Control Gum | Experimental Gum A | Experimental Gum B |
|---|---|---|---|
| Sorbitol | 33.10% | 32.95% | 31.73% |
| Gum base | 31.00% | 31.00% | 30.00% |
| Sorbitol Syrup | 33.40% | 33.40% | 33.00% |
| Glycerin | 0.90% | 0.90% | 0.90% |
| Zinc Lactate | — | 0.10% | 0.10% |
| Encapsulated high intensity sweetener | 0.35% | 0.35% | 1.1% |
| High intensity sweetener | 0.16% | 0.16% | 0.16% |
| Banana flavor | 1.00% | 1.00% | — |
| Peppermint oil | — | — | 3.00% |
| AITC (added to flavor oil) | — | 0.01% | 0.01% |
| Total | 100.0% | 100.0% | 100.0% |

Results

The data in FIGS. 5-7 show no significant difference observed for off-flavor (including astringency) and bitterness between the experimental gum-A and the control gum. No significant difference in sweetness intensity was observed as well.

These results provide evidence that Applicants invention offers a unique, inexpensive, consumer friendly and readily available means for reducing oral malodor associated with VSCs.

c. Breath Freshening Clinical

A randomized, double-blind clinical study was conducted for evaluation of chewing gum containing zinc lactate and allyl isothiocyanate (AITC). A total of 15 subjects met inclusion and exclusion criteria were recruited and completed the study. Subjects were instructed to refrain from oral hygiene, eating and drinking to the testing site. Each subject exhaled his/her breath to a gas chromatograph to analyze for baseline VSC. Subject was then chewed 1 dose of experimental gum (or control gum) for 12 minutes. Subject exhaled his/her breath to the gas chromatograph immediately after chew, and 60, 120 and 180 minutes. Each test was repeated twice. There were at least two days between treatments. Table 6 below shows the clinical testing results.

TABLE 6

Reduction (or increment) of total VSC after treatment

| | Gumbase | Control gum | Test Gum C (0.01% AITC) | Test Gum D (0.01% AITC 0.1% ZL) |
|---|---|---|---|---|
| Baseline | 0% | 0% | 0% | 0% |
| Immediately after chew | 15% | 46%* | 67%* | 87%*† |
| 60 min | −3% | 14% | 32%* | 56%*† |
| 120 min | −44% | −23% | 29%* | 48%*† |
| 180 min | −46% | −27% | 9% | 24%*† |

(*2-tail p < 0.05 compared with baseline; †2-tail p < 0.05 compared with the control gum)

Results

Gum base did not show statistically significant reduction of oral malodor, measured by total concentration of VSCs using a gas chromatograph at 60, 120 and 180 min. The gum base actually increased VSCs by 3%, 44% and 46% at 60, 120 and 180 min, respectively.

Chewing gums containing AITC alone reduced oral malodor by 67%, 32%, 29% and 9% at immediately after chew, 60, 120, and 180 min, respectively.

Chewing the AITC-ZL gum reduced statistically significant amount of total VSCs by 87%, 56%, 48% and 24% at immediately after chew, 60, 120 and 180 min, respectively.

Hence, the results show that in combining an isothiocyanate with a zinc salt reduces the level of each if used individually, providing a good tasting, organoleptically pleasing composition which is effective against multiple VSCs, thereby reducing oral malodor. Further, this combination provides breath freshening benefits after consumption for at least 60 minutes.

In an embodiment, a chewing gum is provided containing less than 0.2% by weight zinc salt, and less than 0.02% by weight isothiocyanate providing breath freshening benefits after consumption to an individual for at least about 2 hours. Gum base materials suitable for use in the practice of this invention are well known in the art and include natural or synthetic gum bases or mixtures thereof. The gum base may be incorporated in the chewing gum product at a concentration of about 10 to about 40 wt. % and preferably about 20 to about 35 wt. %.

Plasticizing/softening agents commonly used in chewing gum compositions are suitable for use in this invention, including gelatin, waxes and mixtures thereof in amounts of about 0.1 to about 5%. The sweetening agent ingredient used in the practice of this invention may be selected from a wide range of materials, and include the same artificial and polyol sweeteners used for the preparation of tablets, beads and lozenges. Polyol sweeteners such as sorbitol and maltitol are present in the chewing gum composition of the invention in amounts of about 40 to about 80 wt. % and preferably about 50 to about 75 wt. %. The artificial sweetener is present in the chewing gum composition of the invention in amounts of about 0.1 to about 2 wt. % and preferably about 0.3 to about 1 wt. %.

An optional coating may also to be applied to any of oral compositions disclosed herein. Coating material appreciated by those skilled in the art include, but are not limited to waxes, shellac, polyols, carboxymethyl cellulose, polyethylene/malic anhydride copolymer or kappa-carrageenan In another embodiment, an oral composition of this invention may further comprise a trigeminal stimulant or sensate including but not limited to menthol and other cooling compounds such as WS-23 and other cooling carboxamide compounds and pungent compounds including but not limiting to capsaicinoids and piperines.

As shown in further detail below, the invention may be provided in various oral compositions. Accordingly, various embodiments of the invention is illustrated, but not limited by, the following Examples.

Example 1

A chewing gum formulation (designated "Compositions E, F & G") containing isothiocyanates and zinc salts.

| Ingredients | E Weight % | F Weight % | G Weight % |
| --- | --- | --- | --- |
| Gum Base | 27.5 | 30.00 | 24.34 |
| Sorbitol | 60.00 | 56.88 | 58.00 |
| Mannitol | 1.00 | — | 3.00 |
| Lycasin/Glycerin | 8.44 | 9.50 | 12.00 |
| Sweetener | 0.80 | 0.85 | 0.80 |
| Flavor | 1.75 | 2.00 | 1.75 |
| Allyl isothiocyanate (AITC) | 0.005 | | 0.01 |
| Benzyl isothiocyanate (BITC) | | 0.02 | |
| 3-morpholinopropyl isothiocyanate | 0.005 | | |
| Zinc lactate | | | 0.10 |
| Zinc citrate | 0.50 | | |
| Zinc acetate | | 0.75 | |

Example 2

This invention is illustrated, but not limited by, compressed tablet formulation (designated "Composition H") containing allyl isothiocyanate and zinc citrate:

| Ingredients | Weight % |
| --- | --- |
| Sorbitol | 97.14 |
| Magnesium Stearate | 1.00 |
| Peppermint Oil | 0.10 |
| Sweeteners | 1.00 |
| Zinc citrate | 0.75 |
| Allyl isothiocyanate (AITC) | 0.01 |

Example 3

This invention is illustrated, but not limited by, the hard candy formulation (designated "Composition I") below:

| Ingredients | Weight % |
| --- | --- |
| Isomalt | 97.83 |
| Xylitol | 1.05 |
| High intensity sweetener | 0.07 |
| Flavor | 0.04 |
| Zinc lactate | 1.00 |
| Phenethyl isothiocyanate | 0.01 |

Example 4

This invention is illustrated but not limited by, the dog biscuit formulation (designated "Composition J"). The dog biscuit was prepared according to conventional techniques; and comprises the following ingredients:

| Ingredients | Weight % |
| --- | --- |
| Ground Wheat | 30.0 |
| Oats & Bran | 17.0 |
| Grits & Seeds | 16.5 |
| Gluten | 7.5 |
| Sugar | 6.0 |
| Fat | 5.0 |
| Aromas, Flavors | 7.5 |
| Vitamins & Minerals | 9.95 |
| Zinc lactate | 0.50 |
| Allyl isothiocyanate (AITC) | 0.05 |

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and applicants intend each of those words to be so interpreted in construing this entire specification.

What is claimed is:

1. An oral composition comprising 0.001 to 1 wt. % of a zinc salt selected from the group consisting of zinc lactate and zinc gluconate, and 0.001 to 1 wt. % allyl isothiocyanate to reduce volatile sulfur compounds in the oral cavity, wherein the ratio of the zinc salt and the allyl isothiocyanate in the oral composition is from about 1:10 to about 20:1 by weight, and wherein the oral composition is a chewing gum or a chewy candy.

2. An oral composition effective in reducing hydrogen sulfide ($H_2S$), methyl mercaptan ($CH_3SH$) and combinations thereof comprising a combination of from about 0.002 to about 2% by weight of zinc lactate and from about 0.001 to about 5% by weight of allyl isothiocyanate in a ratio of about 1:10 to about 20:1 by weight, wherein the oral composition is a chewing gum or a chewy candy.

3. The composition of claim 2 wherein the oral composition further comprises an isothiocyanate selected from the group consisting of phenethyl isothiocyanate (PEITC), benzyl isothiocyanate (BITC) and combinations thereof.

4. A composition of claim 2 wherein the oral composition is uncoated.

5. A method of reducing volatile sulfur compounds selected from group consisting of hydrogen sulfide ($H_2S$), methyl mercaptan ($CH_3SH$), or combinations thereof in the oral cavity, the method comprising consuming or masticating an oral composition having an effective amount of a combination of an organic zinc salt selected from the group consisting of zinc lactate and zinc gluconate and allyl isothiocyanate, wherein the ratio of the organic zinc salt and the allyl isothiocyanate in the oral composition is from about 1:1 to about 20:1 by weight, and wherein the oral composition is a chewing gum or a chewy candy.

6. The method of claim 5 wherein the combination of zinc lactate and allyl isothiocyanate compounds effectively reduce volatile sulfur compounds more than when employed individually.

7. The method of claim 5 in which the oral composition contains an effective amount of the zinc lactate of about 0.002 to about 2% by weight and allyl isothiocyanate of 0.001 to about 5% by weight.

8. The oral composition of claim 1, in which the oral composition contains an effective amount of the zinc salt of about 0.01 to about 0.25 wt. %.

9. The oral composition of claim 1, wherein the combined amount of zinc salt and allyl isothiocyanate is less than 0.50% by weight.

* * * * *